United States Patent [19]

Jang et al.

[11] 4,183,740

[45] Jan. 15, 1980

[54] SOLID COMPOSITIONS OF A LIQUID SURFACTANT AND A PYRAZOLIUM HERBICIDE

[75] Inventors: Choong-Gook Jang, Princeton; Nunzio R. Pasarela, Bridgewater, both of N.J.

[73] Assignee: American Cyanamid Company, Stamford, Conn.

[21] Appl. No.: 867,254

[22] Filed: Jan. 5, 1978

[51] Int. Cl.$^2$ ............................................. A01N 17/08
[52] U.S. Cl. .................................... 71/92; 71/DIG. 1
[58] Field of Search ............................. 71/92, DIG. 1

[56] References Cited

U.S. PATENT DOCUMENTS

| 3,154,397 | 10/1964 | Martin | 71/DIG. 1 |
| 3,882,142 | 5/1975 | Walworth et al. | 71/92 X |
| 3,922,161 | 11/1975 | Walworth et al. | 71/92 |
| 4,082,537 | 4/1978 | Dudkoski | 71/121 |

*Primary Examiner*—Catherine L. Mills
*Attorney, Agent, or Firm*—Harry H. Kline

[57] ABSTRACT

There are provided solid herbicidal compositions comprising a molecular dispersion of a liquid non-ionic surfactant in herbicidal 1,2-dimethyl-3,5-diphenyl-pyrazolium salts, and wherein said compositions may optionally contain inert water-soluble bulking/absorbing agents. There is also provided a method for preparing said compositions by: (a) admixing same at room temperature and then melting said mixture at elevated temperatures; or (b) melting together all components of said compositions at elevated temperatures; and then following either of the above procedures, rapidly cooling said melt to obtain the aforementioned compositions.

9 Claims, No Drawings

SOLID COMPOSITIONS OF A LIQUID SURFACTANT AND A PYRAZOLIUM HERBICIDE

The present invention relates to solid herbicidal compositions comprising, a molecular dispersion of a liquid non-ionic surfactant, octylphenoxy polyethoxy ethanol, in a 1,2-dimethyl-3,5-diphenylpyrazolium salt either in the presence or absence of an inert water-soluble solid bulking/absorbing agent incorporated therein so as to aid in the dispersion and/or binding of said liquid surfactant in said herbicide. The invention further relates to a method for preparing the aforementioned herbicidal compositions by melting the components of the composition and then cooling the same.

In general, the above solid herbicidal composition may be prepared as hereinbelow described in detail. The 1,2-dimethyl-3,5-diphenylpyrazolium salt is heated to or above its melting point, and when completely molten a mixture of the appropriate amount of octylphenoxy polyethoxy ethanol and the optional bulking-/absorbing agent is added at room temperature, but preferably preheated to a temperature approaching that of the molten herbicide. The thus-obtained mixture is stirred for a short period of time, and is then poured or sprayed on a cold surface where it rapidly congeals. If so desired, the above molten mixture may be sprayed into a cold gaseous environment, wherein the individual droplets of said spray congeal while in free flight, and are collected as a fine powder. The solidified composition usually has a waxy, sometimes crystalline, appearance and is quite hard. In this state, said composition may be converted to flakes, granules, prills, beads, and the like, with commercially available equipment. Alternatively, the above melt may be extruded into various shapes and, if desired, by commercially available hot-melt extruders.

The solid particles of said composition obtained by the above processes are free-flowing and dry, and are relatively non-hygroscopic. These compositions also possess good solubility in cold water. An additional advantage of the present composition is that the particles shaped therefrom when packed in containers do not form lumps or cake-up upon storage.

Flowability and resistance to moisture pickup of the above particles of said compositions may be further increased by blending and coating said particles with about 1% to 5% by weight, and preferably about 1% to 3% by weight, of a solid lubricating-drying agent, such as a fumed synthetic silica or a precipitated silica with a particle-size range of between 0.015 micron and 2 microns.

The above liquid non-ionic surfactant, referred to in the specification and claims as "octylphenoxy polyethoxy ethanol" has an average molecular weight of 628; contains an average of 9 to 10 ethylene oxide units, representing 67% by weight of said surfactant. The specific gravity of this surfactant is 1.065 at 25° C.; the viscosity is 240 cps at 25° C. (Brookfield; 12 rpm), and the flash point is >300° F. (TOC).

Unfortunately, conventional formulations of said herbicide possess certain undesirable characteristics. For instance, aqueous concentrated solutions of 1,2-dimethyl-3,5-diphenylpyrazolium salt, especially the methyl sulfate, tend to deposit some of the herbicide in a crystalline form when stored for a period of time, especially when exposed to a cold environment. Once partial crystallization has occurred, such concentrates are then heated and agitated in order to redissolve the deposited solids, before they can be used for the preparation of dilute aqueous sprays. Similarly, conventional solid compositions containing said pyrazolium toxicants have a tendency to form lumps and/or cake when stored in containers and exposed to air, since said pyrazolium salt toxicants are usually quite hygroscopic. Significantly, mechanical blends of the components of the composition of the present invention also result in wet powders and/or pastes, which are not suitable for agricultural use.

In general, the compositions of the present invention may be prepared as follows: From about 43% to 73% by weight, and preferably from 50% to 73% by weight (of the composition) of a 1,2-dimethyl-3,5-diphenylpyrazolium salt, preferably the methyl sulfate salt, is melted at a temperature range of 145° C. to 200° C., and preferably 150° C. to 165° C. To the above molten salt there is added 45% to 27% by weight of octylphenoxy polyethoxy ethanol and 0% to 12% by weight of an inert, solid, water-soluble bulking agent, or 57% to 27% by weight, and preferably 50% to 27% by weight (of the overall composition), of a mixture of octylphenoxy polyethoxy ethanol and an inert, solid, water-soluble bulking/absorbing agent such as α-hydro-Ω-hydroxy-poly(oxyethylene)poly(oxypropylene)poly(oxyethylene) block copolymer of an average molecular weight of 8350 and comprising approximately 80% by weight of poly(oxyethylene)hydrophile and approximately 20% by weight of poly(oxypropylene)hydrophobe, an ethylene oxide (25 mol) adduct of soya sterol, polyethylene glycol of an average molecular weight of 6000 having a melting range 60°–63° C. and a viscosity at 210° F. of 700–900 centistokes, hydroxypropyl methylcellulose having an average molecular weight of 20,000–26,000, a methoxyl percent 27–30, an hydroxypropyl percent 4–12, and a viscosity of a 2% aqueous solution at 20° C. of 50 centistokes, equivalents thereof, and mixtures of the same with the proviso that said mixture cannot contain more than 45% by weight of the total composition of octylphenoxy polyethoxy ethanol. The above mixture is added to the molten herbicide, wherein said mixture has a temperature during the addition in the range between 25° C. and 200° C., and preferably between 150° C. and 165° C. After the addition is completed, the resultant mixture is stirred and heated at a temperature range of 145° C. to 200° C., and preferably 150° C. to 165° C., for a period of time from about 2 to 10 minutes or until a homogeneous melt is obtained. Resultant melt may be used directly in a hot-melt extruder to form various shapes, or may be poured or sprayed on a cold surface where it immediately congeals. Alternatively, said melt may be sprayed into a cold gaseous environment, wherein the individual droplets of said spray congeal while in free flight. The thus-obtained solid may then be formed, if desired, into flakes, granules, beads, prills, and the like, by commercially available equipment. The present composition in its final shape is free-flowing, dry and essentially non-hygroscopic. The flowability and resistance to moisture pickup of the above particles of said composition may further be improved by blending and coating the same with about 1% to 5% by weight, and preferably about 1% to 3% by weight, of a solid lubricating-drying agent, such as a fumed synthetic silica or a precipitated silica having a particle-size range of from 0.015 micron to 2 microns.

Thus, it is obvious that the compositions of the present invention comprise 43% to 73% by weight (of the overall composition) of a 1,2-dimethyl-3,5-diphenylpyrazolium salt, preferably the methyl sulfate salt, 45% to 27% by weight of octylphenoxy polyethoxy ethanol and 12% to 0% of an inert, solid, water-soluble bulking-/absorbing agent.

The above-described solid compositions may also be prepared by pre-blending all components of said composition, excepting the silica lubricant-drying agent, at room temperature and then subjecting said blend to the above melt-cool process.

It should be noted that, when the components of said composition are blended, resultant mixtures are wet powders or pastes, and only after having been subjected to the above-discussed melt-cool process, are they converted in said desired solid waxy composition.

It is unexpectedly found that by the above method of preparation, no appreciable decomposition of the 1,2-dimethyl-3,5-diphenylpyrazolium salt or of the other components takes place, and that the herbicidal compositions obtained by the above method are quite stable at temperatures up to about 100° C. for a prolonged period of time. Thus, the solid compositions of the present invention provide the user ease of handling, avoidance of storage problems, and the elimination of the need for shipping and storing an inert bulk carrier, such as water.

The 1,2-dimethyl-3,5-diphenylpyrazolium salts of the present composition are known. For instance, they have been disclosed in U.S. Pat. No. 3,882,142, issued on May 6, 1975 to Walworth et al. Their use as herbicides has been disclosed in U.S. Pat. No. 3,922,161, issued on Nov. 25, 1975 to Walworth et al. Further, their use as fungicides is disclosed in U.S. Pat. No. 3,930,011, issued on Dec. 30, 1975 to Walworth.

The hereinabove-defined compositions are eminently suitable for the postemergence control of undesired plant species, especially wild oats in the presence of crops such as wheat, barley, oats and rye, when applied at a rate of 0.56 to 3.36 kg per hectare of active cation.

The present invention is further illustrated by the following examples.

EXAMPLE 1

Preparation of a 1,2-Dimethyl-3,5-diphenylpyrazolium Methyl Sulfate-Octylphenoxy Polyethoxy Ethanol Composition.

The 1,2-dimethyl-3,5-diphenylpyrazolium methyl sulfate (73.1 gms) is melted at 165° C. Octylphenoxy polyethoxy ethanol (26.9 gms), preheated to 150° C., is added to the above melt and the resulting mixture stirred a few minutes at 150°–165° C. until it becomes homogeneous. The thus-obtained homogeneous melt is poured into a shallow pan where it immediately congeals to a waxy solid. The solid is flaked, and 50 g of the flaked solid is blended and coated with 3% by weight (1.5 gms) of fumed synthetic silica (particle size: 2 microns).

The above preparation is repeated, except that octylphenoxy polyethoxy ethanol (24.2 g) and α-hydro-Ω-hydroxy-poly(oxyethylene)poly(oxypropylene)-poly(oxyethylene) block copolymer (2.7 g; av. mol. wt. 8350) are mixed, heated to 150° C. until a clear solution is formed, and then this solution is added to the molten 1,2-dimethyl-3,5-diphenylpyrazolium methyl sulfate. After cooling, the resultant waxy solid composition is substantially harder than one prepared without the above bulking/absorbing agent.

EXAMPLES 2 to 7

Preparation of 1,2-Dimethyl-3,5-diphenylpyrazolium Methyl Sulfate-Octylphenoxy Polyethoxy Ethanol Compositions.

Technical 1,2-dimethyl-3,5-diphenylpyrazolium methyl sulfate is melted at 165° C. To the above melt the appropriate amount of octylphenoxy polyethoxy ethanol or a blend of same with the selected bulking/absorbing agent, preheated to 150° C. is added. Resultant mixture is stirred a few minutes at 150°–165° C. until it becomes homogeneous and is then poured on a cold surface where it immediately congeals. The compositions thus-obtained are waxy solids. They are granulated to 10/20 mesh size and one-half of each sample is blended and coated with either a fumed synthetic or precipitated silica (particle size 0.015 to 2 microns). The amounts of each of the components are set forth in Table I, below.

TABLE 1

Compositions of Examples 2 to 7

| Component | Example 2 Percent As Is | Example 2 Percent Real | Example 2 Weight in Grams | Example 3 Percent As Is | Example 3 Percent Real | Example 3 Weight in Grams | Example 4 Percent As Is | Example 4 Percent Real | Example 4 Weight in Grams |
|---|---|---|---|---|---|---|---|---|---|
| 1,2-Dimethyl-3,5-diphenyl-pyrazolium methyl sulfate | 60.3 | 57.9 | 60.3 | 60.3 | 57.9 | 60.3 | 60.3 | 57.9 | 60.3 |
| Octylphenoxy Polyethoxy ethanol | 39.7 | 39.7 | 39.7 | 37.7 | 37.7 | 37.7 | 35.7 | 35.7 | 35.7 |
| α-Hydro-Ω-hydroxy-poly-(oxyethylene)poly(oxypropylene)-poly(oxyethylene) block copolymer | — | — | — | 2.0 | 2.0 | 2.0 | 4.0 | 4.0 | 4.0 |
| Total | 100.0 | — | 100.0 | 100.0 | — | 100.0 | 100.0 | — | 100.0 |

| Component | Example 5 Percent As Is | Example 5 Percent Real | Example 5 Weight in Grams | Example 6 Percent As Is | Example 6 Percent Real | Example 6 Weight in Grams | Example 7 Percent As Is | Example 7 Percent Real | Example 7 Weight in Grams |
|---|---|---|---|---|---|---|---|---|---|
| 1,2-Dimethyl-3,5-diphenyl-pyrazolium methyl sulfate | 60.3 | 57.9 | 60.3 | 60.3 | 57.9 | 60.3 | 60.3 | 57.9 | 60.3 |
| Octylphenoxy polyethoxy ethanol | 33.7 | 33.7 | 33.7 | 29.8 | 29.8 | 29.8 | 29.8 | 29.8 | 29.8 |
| α-Hydro-Ω-hydoxy-poly-(oxyethylene)poly(oxypropylene)- | 6.0 | 6.0 | 6.0 | 9.9 | 9.9 | 9.9 | — | — | — |

TABLE 1-continued

| Compositions of Examples 2 to 7 | | | | | | | | | |
|---|---|---|---|---|---|---|---|---|---|
| poly(oxyethylene) block copolymer Ethylene oxide (25 mol) Adduct of Soya sterol | | — | — | — | — | — | — | 9.9 | 9.9 | 9.9 |
| Total | 100.0 | | 100.0 | 100.0 | | 100.0 | 100.0 | | 100.0 |

EXAMPLES 8 to 12

Preparation of 1,2-Dimethyl-3,5-diphenylpyrazolium Methyl Sulfate-Octylphenoxy Polyethoxy Ethanol Compositions.

The method described in Examples 2 to 7 is employed to prepare the compositions tabularized in Table II, below, except that:

(a) Various bulking/absorbing agents and combinations thereof are used; and (b) The composition of Examples 12 is extruded at 165° C. to form flakes.

EXAMPLES 13 to 17

Preparation of 1,2-Dimethyl-3,5-diphenylpyrazolium Methyl Sulfate-Octylphenoxy Polyethoxy Ethanol Compositions.

The components of the composition as hereinbelow defined in Table III are blended at room temperature. The thus-obtained mixtures which are slurries or pastes are heated at 165° C. until homogeneous melts are formed. The latter melts are extruded and then chopped into granules of less than 10 mesh size.

Alternatively, a melt of the composition as obtained above is sprayed through a nozzle into air at room temperature. The smaller droplets of the spray congeal while in free flight and are subsequently collected as a fine dust. The larger droplets impact on a cold surface, where they congeal, and are then collected and screened to less than 8 mesh.

TABLE II

| | Compositions of Examples 8 to 12 | | | | | |
|---|---|---|---|---|---|---|
| | Example 8 | | | Example 9 | | |
| | Percent | | Weight | Percent | | Weight |
| Component | As Is | Real | in Grams | As Is | Real | in Grams |
| 1,2-Dimethyl-3,5-diphenyl-pyrazolium methyl sulfate | 43.4 | 41.7 | 43.4 | 43.4 | 41.7 | 43.4 |
| Octylphenoxy polyethoxy ethanol | 45.0 | 45.0 | 45.0 | 45.0 | 45.0 | 45.0 |
| Polyethylene glycol Av. Mol. Wt. 6000 | — | — | — | 11.6 | 11.6 | 11.6 |
| Hydroxypropyl methylcellulose; Av. Mol. Wt. 20–26,000 | 11.6 | 11.6 | 11.6 | — | — | — |
| Total | 100.0 | | 100.0 | 100.0 | | 100.0 |

| | Example 10 | | | Example 11 | | | Example 12** | | |
|---|---|---|---|---|---|---|---|---|---|
| | Percent | | Weight | Percent | | Weight | Percent | | Weight |
| Component | As Is | Real | in Grams | As Is | Real | in Grams | As Is | Real | in Grams |
| 1,2-Dimethyl-3,5-diphenyl-pyrazolium methyl sulfate | 73.1 | 70.2 | 46.2 | 50.6 | 48.6 | 101.2 | 73.1 | 70.2 | 1462.0 |
| Octylphenoxy polyethoxy ethanol | 26.9 | 26.9 | 53.8 | 35.0 | 35.0 | 70.0 | 26.9 | 26.9 | 538.0 |
| α-Hydro-Ω-hydroxy-poly-(oxyethylene)poly(oxypropylene)-poly(oxyethylene) block copolymer | — | — | — | 7.2 | 7.2 | 14.4 | — | — | — |
| Hydroxypropyl methylcellulose; Av. Mol. Wt. 20–26,000 | — | — | — | 7.2 | 7.2 | 14.4 | — | — | — |
| Total | 100.0 | — | 200.0 | 100.0 | — | 200.0 | 100.0 | — | 2000.0 |

*Exact composition unknown.
**Extruded at 165° C.

TABLE III

| | Examples | | | | |
|---|---|---|---|---|---|
| | 13 | 14 | 15 | 16 | 17 |
| Component | Percent by Weight | Percent by Weight | Percent by Weight | Percent by Weight | Percent by Weight |
| 1,2-Dimethyl-3,5-diphenyl-pyrazolium methyl sulfate; 98% Technical (cation) | 50.59 (34.29) | 50.59 (34.29) | 51.09 (34.63) | 51.09 (34.63) | 73.1 (47.58) |
| Octylphenoxy polyethoxy ethanol | 34.31 | 34.31 | 34.65 | 34.65 | 26.9 |
| Polyethylene glycol Av. Mol. Wt. 6000 | — | 14.12 | — | — | — |
| Hydroxypropyl methylcellulose Av. Mol. Wt. 20–26,000 | — | — | 7.13 | 14.26 | — |
| α-Hydro-Ω-hydroxy-poly(oxy- | 14.12 | — | 7.13 | — | — |

TABLE III-continued

| Component | Examples | | | | |
|---|---|---|---|---|---|
| | 13 Percent by Weight | 14 Percent by Weight | 15 Percent by Weight | 16 Percent by Weight | 17 Percent by Weight |
| ethylene)poly(oxypropylene)poly-(oxyethylene) block copolymer Av. Mol. Wt. 8350 | | | | | |
| Synthetic, fumed silica, 0.015 to 2 microns | 0.98 | 0.98 | — | — | — |
| Dissolution time in water (95% at 6°-8° C.), in minutes | —* | 3 | 6 | 7 | 0.5** |

*During the chopping operation, the composition picked up moisture and became lumpy.
**Fine dust, congealed in free flight.

We claim:

1. A solid, particulated herbicidal composition comprising from about 27% to about 40%, by weight, of octylphenoxy polyethoxy ethanol and 73% to 60%, by weight, of 1,2-dimethyl-3,5-diphenylpyrazolium salt.

2. The composition according to claim 1, wherein the 1,2-dimethyl-diphenylpyrazolium salt is 1,2-dimethyl-3,5-diphenylpyrazolium methyl sulfate.

3. The composition according to claim 1, comprising a molecular dispersion of from 57% to 27%, by weight, of a mixture of octylphenoxy polyethoxy ethanol and an inert solid water-soluble bulking or absorbing agent selected from the group consisting of α-hydro-Ω-hydroxy-poly(oxyethylene)poly(oxypropylene)-poly(oxyethylene) block copolymer of an average molecular weight of 8350, an ethylene oxide (25 mol) adduct of soya sterol, polyethylene glycol of an average molecular weight of 6000, hydroxypropyl methylcellulose of an average molecular weight of 20,000–26,000, and mixtures thereof; and from 43% to 73%, by weight, of a herbicidal 1,2-dimethyl-3,5-diphenylpyrazolium salt, with the proviso that said composition cannot contain more than 45%, by weight, of octylphenoxy polyethoxy ethanol; and wherein said particulated herbicidal composition may optionally be blended and coated with 1% to 5%, by weight, of said composition of fumed synthetic or precipitated silica having a particle-size range of 0.015 micron to 2 microns.

4. The composition according to claim 1 comprising 73%, by weight, of 1,2-dimethyl-3,5-diphenylpyrazolium methyl sulfate and 27% by weight of octylphenoxy polyethoxy ethanol.

5. The composition according to claim 1 comprising 60%, by weight, of 1,2-dimethyl-3,5-diphenylpyrazolium methyl sulfate and 40%, by weight, of octylphenoxy polyethoxy ethanol.

6. The composition according to claim 3 comprising 50% to 52%, by weight, of 1,2-dimethyl-3,5-diphenylpyrazolium salt, 35% to 34%, by weight, of octylphenoxy polyethoxy ethanol and 15% to 14%, by weight, of said bulking or absorbing agent.

7. The composition according to claim 3 comprising from 50% to 52%, by weight, of 1,2-dimethyl-3,5-diphenylpyrazolium methyl sulfate, from 35% to 34%, by weight, of octylphenoxy polyethoxy ethanol and from 15% to 14%, by weight, of polyethylene glycol of an average molecular weight of 6000.

8. The composition according to claim 3 comprising from 50% to 52%, by weight, of 1,2-dimethyl-3,5-diphenylpyrazolium methyl sulfate, from 7.5% to 7%, by weight, of α-hydro-Ω-hydroxy-poly(oxyethylene)-poly(oxypropylene)poly(oxyethylene) block copolymer of an average molecular weight of 8350 and 7.5% to 7% by weight of hydroxypropyl methylcellulose of an average molecular weight of 20,000 to 26,000.

9. A method for the preparation of a solid herbicidal composition according to claim 3 comprising blending from 57% to 27%, by weight, of a mixture of the liquid non-ionic surfactant octylphenoxy polyethoxy ethanol and an inert solid water-soluble bulking/absorbing agent selected from the group consisting of α-hydro-Ω-hydroxy-poly(oxyethylene)poly(oxypropylene)-poly(oxyethylene) block copolymer of an average molecular weight of 8350, an ethylene oxide (25 mol) adduct of soya sterol, polyethylene glycol of an average molecular weight of 6000, hydroxypropyl methylcellulose of an average molecular weight of 20,000–26,000 and mixtures thereof, with 43% to 73% by weight of a herbicidal 1,2-dimethyl-3,5-diphenylpyrazolium salt, with the proviso that said overall blend cannot contain more than 45% by weight of octylphenoxy polyethoxy ethanol; heating resultant blend at from 145° C. to 200° C. for a period of time sufficient to obtain a homogeneous melt, and rapidly lowering the temperature of said melt until it congeals to a waxy solid.

* * * * *